(12) United States Patent
Maeda (10) Patent No.: US 6,738,134 B2
(45) Date of Patent: May 18, 2004

(54) INSPECTION METHOD AND INSPECTION SYSTEM OF A TERMINAL METAL FITTING

(75) Inventor: Tatsuya Maeda, Shizuoka (JP)

(73) Assignee: Yazaki Corporation, Tokyo (JP)

( * ) Notice: Subject to any disclaimer, the term of this patent is extended or adjusted under 35 U.S.C. 154(b) by 0 days.

(21) Appl. No.: 09/963,575

(22) Filed: Sep. 27, 2001

(65) Prior Publication Data

US 2002/0036770 A1 Mar. 28, 2002

(30) Foreign Application Priority Data

Sep. 28, 2000 (JP) ......................................... 2000-296332

(51) Int. Cl.⁷ .............................................. G01N 21/88
(52) U.S. Cl. ...................... 356/237.2; 356/628; 250/625
(58) Field of Search ................. 356/237.1, 237.2–237.5, 356/394, 628; 250/559.34, 559.19–559.26; 382/149, 141–151

(56) References Cited

U.S. PATENT DOCUMENTS

| | | | |
|---|---|---|---|
| 4,555,799 A | * 11/1985 | Kodama et al. | 382/141 |
| 5,058,178 A | 10/1991 | Ray | |
| 5,377,278 A | * 12/1994 | Ichikawa | 382/145 |
| 5,757,955 A | * 5/1998 | Fujisawa et al. | 382/141 |
| 5,774,574 A | * 6/1998 | Hoki | 702/35 |
| 5,899,959 A | * 5/1999 | Shields et al. | 382/149 |
| 6,047,084 A | * 4/2000 | Kent et al. | 382/147 |

FOREIGN PATENT DOCUMENTS

| | | |
|---|---|---|
| EP | 0 562 614 A | 9/1993 |
| EP | 0 702 227 A | 3/1996 |
| JP | 10-154568 | 6/1998 |

\* cited by examiner

Primary Examiner—Richard A. Rosenberger
Assistant Examiner—Vincent P. Barth
(74) Attorney, Agent, or Firm—Armstrong, Kratz, Quintos, Hanson & Brooks, LLP.

(57) ABSTRACT

An inspection method and an inspection system of a terminal metal fitting which can securely judge the good or bad of the fastening condition of an electric wire by a crimping piece of the terminal metal fitting is provided. The inspection system 1 of the terminal metal fitting has an illuminating lamp 4, a CCD camera 5, a dark box 6, and a control unit 7. The CCD camera 5 is arranged at a position of the light thrown from the illuminating lamp 4 and reflected by crimping pieces 212a,212b of a pressure welding terminal 200 not entering the CCD camera 5. The dark box 6 covers the illuminating lamp 4, an object side 5a of the CCD camera 5, and the pressure welding terminal 200. The control unit 7 makes a binary processing on an image of a wire connecting portion 204 taken by the CCD camera 5. The control unit 7 is provided on each of the crimping pieces 212a,212b and judges the good or bad of the crimping condition on the basis of an area in black in an inspection area in the binary image of at least some part of the crimping piece.

8 Claims, 10 Drawing Sheets

INSPECTION METHOD AND INSPECTION SYSTEM OF A TERMINAL METAL FITTING

BACKGROUND OF THE INVENTION

1. Field of the invention

The present invention relates to an inspection method and an inspection system of a terminal metal fitting for judging the good or bad of the fastening condition of an electric wire by a crimping piece of the terminal metal fitting.

2. Description of the Related Art

A wiring harness is arranged on a motor vehicle in order to supply electric power from power source such as a battery to onboard equipment such as various kinds of lamps or motors. The above wiring harness has a plurality of electric wires, a pressure welding terminal as a terminal metal fitting attached to an end portion of each electric wire, and a connector housing accommodating the pressure welding terminal.

The above pressure welding terminal has a wire connecting portion which it is electrically connected to the above electric wire and fastens it. The above wire connecting portion has a wall carrying the above electric wire, a pressure welding portion pressure-welded to the above electric wire and a crimping piece. The pressure welding portion has a pair of press-fit blades to press the electric wire therebetween.

The electric wire is pressed into a pair of press-fit blades, the above press-fit blades cut into a sheathing portion of the electric wire and are put into contact with a core wire, and then the above pressure welding portion is electrically connected to the electric wire. Crimping pieces are stood on respective edges of the above wall. The crimping pieces each are bent toward the above wall, and the electric wire placed on the above wall is fastened by the crimping pieces.

The above-described pressure welding terminal is inserted in a terminal accommodating groove of the connector housing of insulative synthetic resin, and the electric wire is pressed between press-fit blades. When the electric wire is pressed into press-fit blades, a well-known pressure welding apparatus is used.

The above pressure welding apparatus has a pressure welding blade of metal and a pair of guides to guide the pressure welding blades. First, the wire connecting portion is sandwiched between the guides. Subsequently, the pressure welding blade presses the electric wire into press-fit blades and bends the crimping pieces toward the above wall.

With respect to the above prior art pressure welding apparatus, however, when the electric wire is pressed into press-fit blades, that is, when the electric wire is pressure-welded to the wire connecting portion, the above guide is likely to get out of position, and therefore the pressure welding blade is not often put into contact with the crimping piece.

And, when the connector housing has a plurality of pressure welding terminals in parallel, if the guide makes a position divergence, the above pressure welding blade would be put into contact with a crimping piece of the adjoining pressure welding terminal instead of the aiming pressure welding terminal. In this case, the crimping piece of the adjoining pressure welding terminal is reversely bent outwardly, thereby not fastening the electric wire.

And, a visual inspection has been conventionally carried out in order to judge the good or bad of the fastening condition of the electric wire by the crimping piece of the pressure welding terminal. In the visual inspection, a defective could be judged to be a non-defective by skill level of a worker, and a judgement of the good or bad would be different at every worker, thereby judging a defective to be a non-defective. This caused an assembly of a defective on the wiring harness.

SUMMARY OF THE INVENTION

In view of the foregoing, an object of the present invention to provide an inspection method and an inspection system of a terminal metal fitting which can securely judge the good or bad of the fastening condition of an electric wire by a crimping piece of the terminal metal fitting.

In order to achieve the above object, as a first aspect of the present invention, an inspection method of a terminal metal fitting having an wire connecting portion having a wall carrying an electric wire and a crimping piece bent toward the wall so as to fasten the electric wire between the crimping piece and the wall comprises the steps of: illuminating the wire connecting portion fastened to the electric wire; binary-processing an image of the wire connecting portion illuminated; calculating an area less than or not less than a threshold value in image information obtained by the binary processing; and judging good or bad of a fastening condition of the electric wire by the crimping piece on a basis of the area.

As a second aspect of the present invention, an inspection system of a terminal metal fitting having an wire connecting portion having a wall carrying an electric wire and a crimping piece bent toward the wall so as to fasten the electric wire between the crimping piece and the wall comprises: a light source to illuminate the wire connecting portion; an image-taking means to take an image of the wire connecting portion; a dark box, with a dark inner surface, to cover at least an object side of the image-taking means, the light source, and the terminal metal fitting for preventing outer light from shining on the wire connecting portion; and a judging means to binary-process an image of the wire connecting portion illuminated by the light source and judge good or bad of a fastening condition of the electric wire by the crimping piece on a basis of an area less than or not less than a threshold value in image information obtained by the binary processing, wherein the image-taking means and the light source are arranged so that the light thrown from the light source and reflected by the crimping piece does not enter the image-taking means, and a sheathing portion of the electric wire is a light color.

As a third aspect of the present invention, based on the second aspect, the image-taking means faces the wall of the wire connecting portion to which the electric wire is fastened, and the light source is arranged at a position of making an angle θ between a line connecting the light source with the crimping piece and a direction of the electric wire fastened to the wire connecting portion so that the light thrown from the light source and reflected by the crimping piece does not enter the image-taking means.

As a fourth aspect of the present invention, based on the third aspect, the light source is arranged at a position of making the angle θ of not more than 45 degrees.

As a fifth aspect of the present invention, an inspection system of a terminal metal fitting having an wire connecting portion having a wall carrying an electric wire and a crimping piece bent toward the wall so as to fasten the electric wire between the crimping piece and the wall comprises: a light source to illuminate the wire connecting portion; an image-taking means to take an image of the wire connecting portion; a judging means to binary-process an image of the wire connecting portion illuminated by the light source and judge good or bad of a fastening condition of the electric wire by the crimping piece on a basis of an area less than or not less than a threshold value in image information obtained by the binary processing, wherein the image-taking means and the light source are arranged so that the light thrown from the light source and reflected by the crimping piece enters the image-taking means.

As a sixth aspect of the present invention, based on the fifth aspect, the image-taking means faces the wall of the wire connecting portion to which the electric wire is fastened, and the light source faces the wall of the wire connecting portion, to which the electric wire is fastened, near the image-taking means so that the light thrown from the light source and reflected by the crimping piece enters the image-taking means.

As a seventh aspect of the present invention, based on any one of the second to sixth aspects, the judging means judges good or bad of a fastening condition of the electric wire on a basis of an area less than or not less than a threshold value in an inspection area in the image of the wire connecting portion taken by the image-taking means, the inspection area being provided for each crimping piece and including at least partial image of the crimping piece.

As an eighth aspect of the present invention, based on the seventh aspect, the inspection area is positioned over a longitudinal axis of the electric wire fastened to the wire connecting portion.

According to the above-described structures of the present invention, the following advantages are provided.

(1) Because the intensity of the reflected light of the terminal metal fitting and the electric wire is different when the wire connecting portion is illuminated, the crimping piece and the electric wire can be distinguished by binary-processing the image of the crimping piece. Because states of the crimping pieces, that is, standing perpendicularly to the wall, being bent outwardly of the wire connecting portion, and being bent inwardly toward the wall while fastening the electric wire, can be easily distinguished, the good or bad of the fastening condition of the electric wire by the crimping piece can be easily judged. Therefore, on the basis of an area not less than or less than the threshold value in the binary image, the good or bad of the fastening condition of the electric wire by the crimping piece can be securely judged.

(2) Viewing from the image-taking means, the dark inner surface of the dark box is reflected in the crimping piece and the sheathing portion of the electric wire is a light color. Therefore, when the image of the wire connecting portion obtained by the image-taking means is binary-processed, the electric wire securely becomes "not less than the threshold value" and the crimping piece securely becomes "less than the threshold value". Therefore, the electric wire and the crimping piece can be more securely distinguished. Therefore, on the basis of an area not less than or less than the threshold value in the binary image, the good or bad of the fastening condition of the electric wire by the crimping piece can be more securely judged.

(3) The light source is arranged at a position of making an angle between the line connecting the light source with the crimping piece and the direction of the electric wire fastened to the wire connecting portion. Therefore, because the light thrown from the light source and reflected by the crimping piece does not securely enter the image-taking means, when the image of the wire connecting portion obtained by the image-taking means is binary-processed, the electric wire and the crimping piece can be more securely distinguished. Therefore, on the basis of an area not less than or less than the threshold value in the binary image, the good or bad of the fastening condition of the electric wire by the crimping piece can be still more securely judged.

(4) The light source is arranged at a position of the angle of not more than 45 degrees. Therefore, because the light thrown from the light source and reflected by the crimping piece does not securely enter the image-taking means, when the image of the wire connecting portion obtained by the image-taking means is binary-processed, the electric wire and the crimping piece can be more securely distinguished. Therefore, on the basis of an area not less than or less than the threshold value in the binary image, the good or bad of the fastening condition of the electric wire by the crimping piece can be still more securely judged.

(5) The image-taking means and the light source are arranged so that the light thrown from the light source and reflected by the crimping piece enters the image-taking means. Therefore, when the image of the wire connecting portion obtained by the image-taking means is binary-processed, the electric wire securely becomes "less than the threshold value" and the crimping piece securely becomes "not less than the threshold value". Therefore, the electric wire and the crimping piece can be more securely distinguished. Therefore, on the basis of an area not less than or less than the threshold value in the binary image, the good or bad of the fastening condition of the electric wire by the crimping piece can be more securely judged.

(6) The image-taking means and the light source face the wall of the wire connecting portion, and the light source is arranged near the image-taking means. Therefore, because the light thrown from the light source and reflected by the crimping piece securely enters the image-taking means, when the image of the wire connecting portion obtained by the image-taking means is binary-processed, the electric wire and the crimping piece can be more securely distinguished. Therefore, on the basis of an area not less than or less than the threshold value in the binary image, the good or bad of the fastening condition of the electric wire by the crimping piece can be still more securely judged.

(7) The judging means judges the fastening condition of the electric wire by the crimping pieces on the basis of an area, corresponding to each crimping piece, of not less than or less than the threshold value in the inspection area. Therefore, the fastening condition of the electric wire can be more unerringly judged than a case of providing one large inspection area over a plurality of crimping pieces.

(8) Because the inspection area is positioned over the center of the electric wire, an area not less than the threshold value and an area less than the threshold value of the inspection area sensitively vary according to the good or bad of the crimping piece. Therefore, the electric wire and the crimping piece can be still more securely distinguished. And, on the basis of an area not less than or less than the threshold value in the binary image, the good or bad of the fastening condition of the electric wire by the crimping piece can be still more unerringly and securely judged.

The above and other objects and features of the present invention will become more apparent from the following description taken in conjunction with the accompanying drawings.

DESCRIPTION OF THE PREFERRED EMBODIMENT(S)

Figure 1:
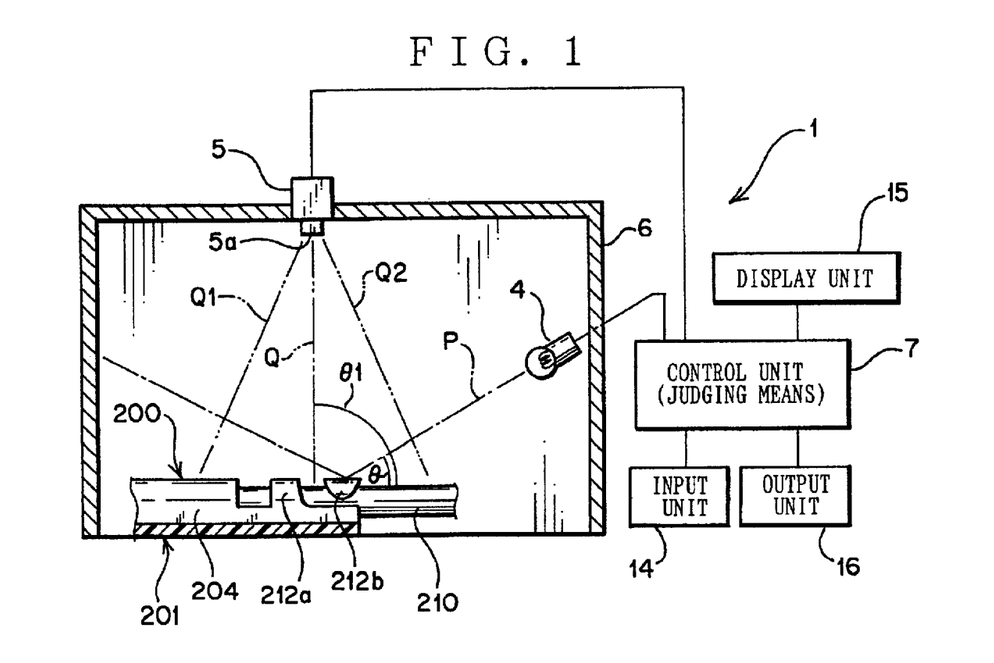
FIG. 1 is a schematic diagram showing the structure of a inspection system of a terminal metal fitting in accordance with a first embodiment of the present invention.
Figure 2:
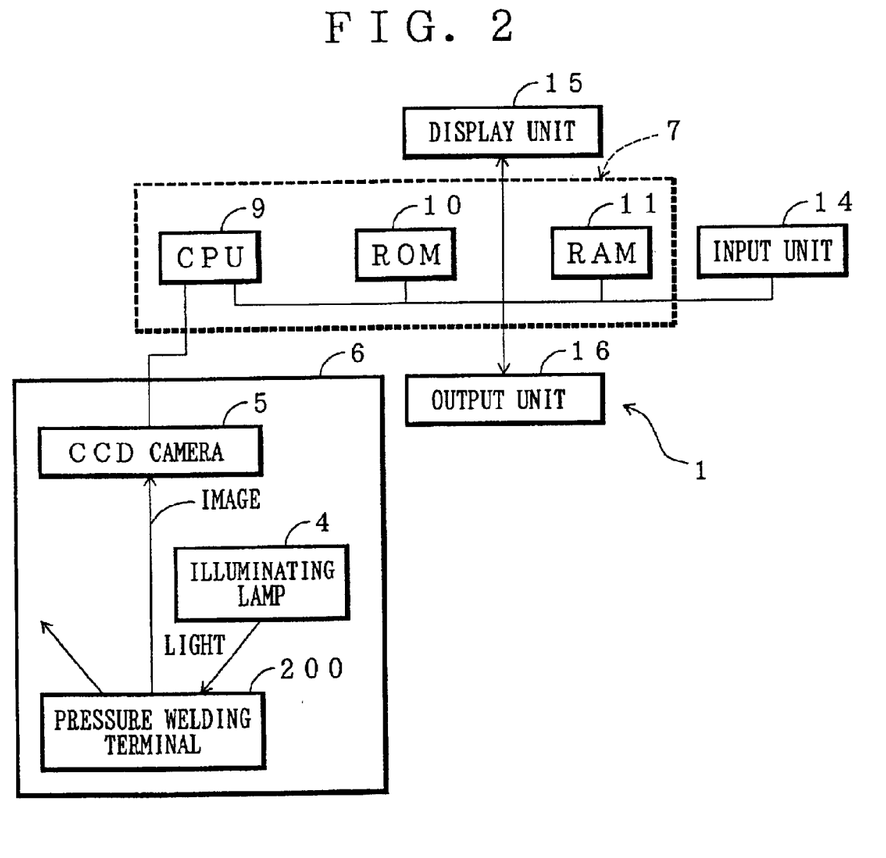
FIG. 2 is a block diagram of the inspection system shown in FIG. 1.

Embodiment(s) of the present invention will now be described in further detail with reference to the accompanying drawings. The inspection system 1 of the terminal metal fitting in accordance with a first embodiment of the present invention is described by making reference to FIG. 1 to FIG. 10. The inspection system 1 shown in FIG. 1 and FIG. 2 is a system which inspects the fastening condition of the electric wire 210 by a later-described crimping pieces 212a, 212b of the pressure welding terminal 200 after having pressure-welded the electric wire 210 to the pressure welding terminal 200 as a terminal metal fitting shown in FIG. 10.

The inspection system 1 carries out an inspection after the pressure welding terminal 200 is attached to the connector housing 201 (FIG. 10) and the electric wire 210 is pressure-welded. And, in the present embodiment, the sheathing portion of the electric wire 210 is light colors such as white, light water color, or light yellow for example.

Figure 10:
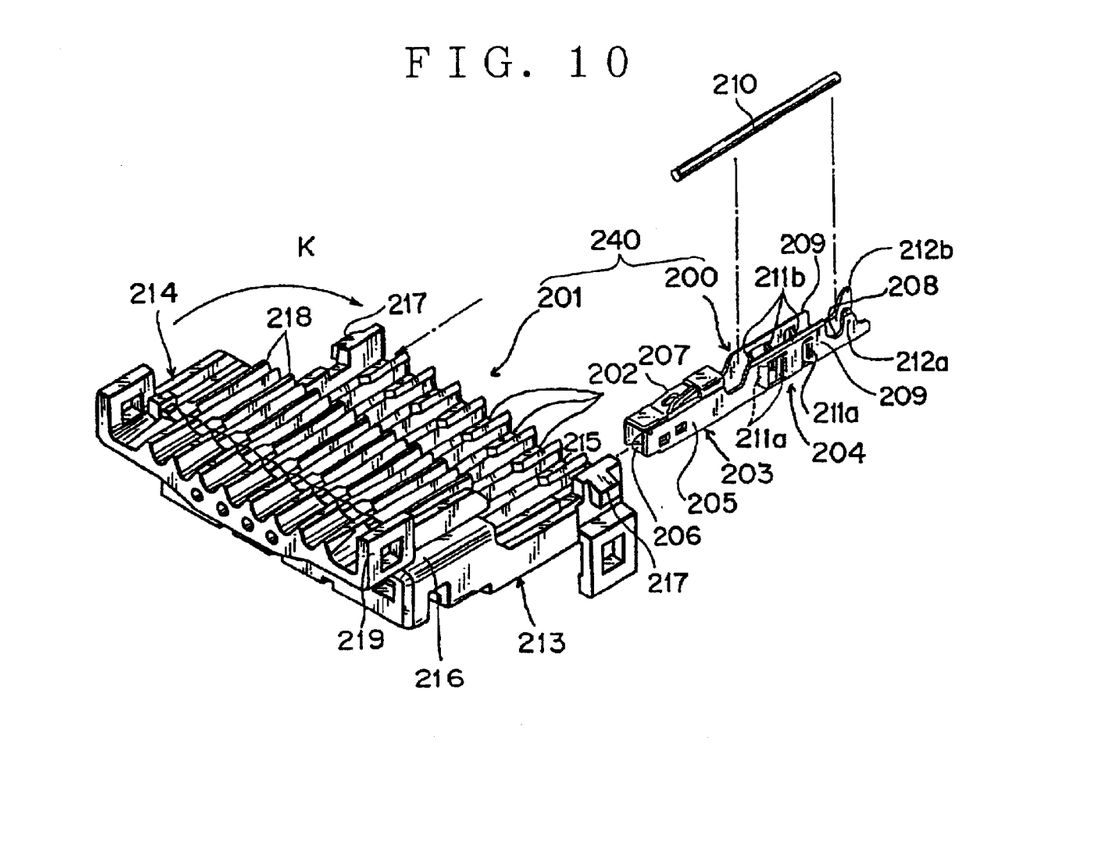
FIG. 10 is a perspective view showing a pressure welding terminal inspected by the inspection system of the present invention and a connector housing for accommodating the pressure welding terminal.

The pressure welding terminal 200 is formed by bending a conductive metal plate. The above conductive metal plate is tin-plated. That is, the pressure welding terminal 200 is so-called a tin-plated terminal. Therefore, the pressure welding terminal 200 has a mirror-like surface. The pressure welding terminal 200 has the electric contact portion 203 and the wire connecting portion 204 as shown in FIG. 10.

The electric contact portion 203 has the tube portion 205, the elastic contact piece 206 to connect with a non-shown male terminal and the lance 207 to engage the connector housing 201. The tube portion 205 continues to a later-described wall 208 and a sidewall 209 of the wire connecting portion 204. The elastic contact piece 206 is provided in the tube portion 205 to push a male terminal inserted into the tube portion 205 toward the inner surface of the tube portion 205 for preventing the male terminal from coming out of the tube portion 205.

The lance 207 is provided on the outside surface of the tube portion 205 like a belt. One end portion of the lance 207 continues with the tube portion 205, and the other end portion is contactable and discountable with the tube portion 205 elastically deformably. The lance 207 engages the connector housing 201 and prevents the pressure welding terminal 200 from coming out of the terminal accommodating groove 202.

The wire connecting portion 204 has the wall 208 carrying the electric wire 210, a pair of sidewalls 209, three pairs of press-fit blades 211a, 211b and a pair of crimping pieces 212a, 212b facing each other. The wall 208 is formed rectangularly. The sidewalls 209 continue from the wall 208. The sidewall 209 is oppositely stood from the wall 208.

The three pairs of press-fit blades 211a, 211b projects from the sidewalls 209. Each pair of press-fit blades 211a, 211b face each other. When the electric wire 210 is pressed between the pair of press-fit blades 211a,211b, the pair of press-fit blades 211a, 211b cut the sheathing portion of the electric wire 210 and are put into contact with the core wire of the electric wire 210. That is, the three pairs of press-fit blades 211a, 211b are pressure-welded with the electric wire 210 and electrically connected therewith.

A pair of crimping pieces 212a, 212b are each stood on the wall 208. The crimping pieces 212a, 212b are bent toward the wall 208 so that the electric wire 210 can be held between the crimping pieces 212a, 212b and the wall 208. Like this, the crimping pieces 212a, 212b fastens the electric wire 210 to the wire connecting portion 204.

The connector housing 201 is made of white insulative synthetic resin. The connector housing 201 has the terminal accommodating portion 213 and the cover 214 connected with the terminal accommodating portion 213 through a hinge as shown in FIG. 10.

The terminal accommodating portion 213 has the generally rectangular plate portion 215, a plurality of terminal accommodating grooves 202 and the ceiling wall 216 spacedly facing the plate portion 215. The plate portion 215 has non-shown lock groove and locking arm which prevent the pressure welding terminal 200 inserted in the terminal accommodating groove 202 from coming out.

The terminal accommodating grooves 202 are arranged in parallel on the surface of the plate portion 215. The terminal accommodating groove 202 extends substantially straight, and the pressure welding terminal 200 is longitudinally inserted therein.

The ceiling wall 216 is formed generally rectangularly and covers the electric contact portion 203, while exposing the wire connecting portion 204 of the pressure welding terminal 200 accommodated in the terminal accommodating groove 202. And, a pair of engaging projections 217 outwardly projecting are provided on the opposite side of the ceiling wall 216.

The cover 214 has wire-holding projecting strips 218 to face the respective terminal accommodating grooves 202 of the terminal accommodating portion 213. The cover 214 has a pair of cover-locking arms 219 engagable with the respective engaging projections 217. The cover 214 is turnable with respect to the terminal accommodating portion 213 by a non-shown hinge provided at the edge portion of the above ceiling wall 216.

Before the assembly, the above-described connector housing 201 is connected with the cover 214 through a non-shown band in a state that the cover 214 is reversed with respect to the terminal accommodating portion 213.

And, the pressure welding terminal 200 is firstly inserted in the terminal accommodating groove 202. And, the lance 207 engages the connector housing 201, and the pressure welding terminal 200 is held in the connector housing 201. The electric wire 210 is pressed between press-fit blades 211a,211b, and the crimping pieces 212a, 212b are bent to fasten the electric wire 210.

Subsequently, the inspection of the crimping condition, that is, the fastening condition of the electric wire 210 by the crimping pieces 212a, 212b is carried out by the inspection system 1. The band is removed when it is judged that the fastening condition of all the electric wires 210 by the respective pairs of crimping pieces 212a, 212b of the pressure welding terminals 200 is good, and the cover 214 is turned in an arrow K direction about the hinge.

The cover-locking arms 219 engage the engaging projections 217, and the terminal accommodating portion 213 and the cover 214 are fixed to each other in a state that the projecting strips 218 agree with the terminal accommodating grooves 202. Here, the pressure welding terminal 200 and the connector housing 201 constitute the connector 240. And, when it is judged the fastening condition of at least one crimping piece is failure, the connector 240 is judged to be a defective.

The inspection system 1 has the illuminating lamp 4 as the light source, the CCD camera 5 as an image-taking means, the dark box 6, the control unit 7 as a judging means, the input unit 14, the display unit 15 and the output unit 16 as shown in FIG. 1 and FIG. 2.

The illuminating lamp 4 illuminates the wire connecting portion 204 of the pressure welding terminal 200 inserted in the terminal accommodating groove 202 of the connector housing 201 and fastened to the electric wire 210. The illuminating lamp 4 is arranged at a position of making an angle θ between the optical axis P and the wall 208, namely the direction of the electric wire 210. And, the illuminating lamp 4 is desirably arranged at a position of making the angle θ of not more than 45 degrees.

Here, the above optical axis P is a line connecting the illuminating lamp 4 and the crimping pieces 212a,212b. In the illustrated embodiment, the illuminating lamp 4 is arranged at a position of making the above angle θ being 40 degrees. As the illuminating lamp 4, a well-known high luminance halogen lamp may be used for example.

The CCD camera 5 can image-take the wire connecting portion 204 of the pressure welding terminal 200 inserted in the terminal accommodating groove 202 of the connector housing 201. The CCD camera 5 can image-take a range between the two-dot chain lines Q1, Q2 in FIG. 1.

The CCD camera 5 is arranged at a position facing or over the wall 208 and the normally crimped crimping pieces 212a,212b. In the illustrated embodiment, the CCD camera 5 is arranged at a position of making the angle θ 190 degrees. The angle θ 1 is formed between the optical axis Q and the wall 208.

The CCD camera 5 has two-dimensional CCD image sensor elements having two-dimensionally arranged image sensor elements and a lens to lead the image to the two-dimensional CCD image sensor elements. The two-dimensional CCD image sensor elements can sense the strength and weakness of the light. That is, the CCD camera 5 senses the strength and weakness of the light. The CCD camera 5 image-takes a so-called monochrome image with concentration difference.

With the above-described the structure, the illuminating lamp 4 and the CCD camera 5 are arranged so that the light from the illuminating lamp 4 reflected by the crimping pieces 212a, 212b of the pressure welding terminal 200 as an inspection object does not enter the CCD camera 5.

The dark box 6 accommodates the illuminating lamp 4, an object side 5a of the lens of the CCD camera 5, and the pressure welding terminal 200 as the inspection object. The inner surface of the dark box 6 is dark color such as black, dark blue, dark green for example.

The input unit 14 is used to input an article number, the number and the like of the pressure welding terminal 200 as the inspection object into the control unit 7. As the input unit 14, well-known keyboard, mouse, various switches and operation buttons may be used.

The display unit 15 displays operation conditions of the inspection system 1, the good or bad of the inspected pressure welding terminal 200 and the like. As the display unit 15, well-known CRT (Cathode Ray Tube) display or liquid crystal display may be used.

The output unit 16 outputs the good or bad of the pressure welding terminal 200 inspected by the inspection system 1. As the output unit 16, well-known printer to print the above inspection results or CD-ROM drive assembly writable of the above inspection result as electronic information on the CD-ROM may be used.

The control unit 7 is a computer having a well-known CPU (Central Processing Unit) 9, a ROM (Read-only Memory) 10, and a RAM (Random Access Memory) 11 as shown in FIG. 2. The control unit 7 is connected to the illuminating lamp 4, the CCD camera 5, the input unit 14, the display unit 15, and the output unit 16. The control unit 7 controls the illuminating lamp 4, the CCD camera 5, the input unit 14, the display unit 15, and the output unit 16, that is, controls the entire inspection system 1.

The control unit 7 takes in the image of the wire connecting portion 204 taken by the CCD camera 5 and saves it. Here, the image is a digital image of the two-dimensionally arranged elements each exhibiting the light intensity of 256 levels for example.

The control unit 7 carries out a binary processing with a predetermined threshold value on the image of the wire connecting portion 204. Here, the threshold value of the binary processing is suitably decided according to the light intensity of the illuminating lamp 4 and the article number of the pressure welding terminal 200.

Figure 4:
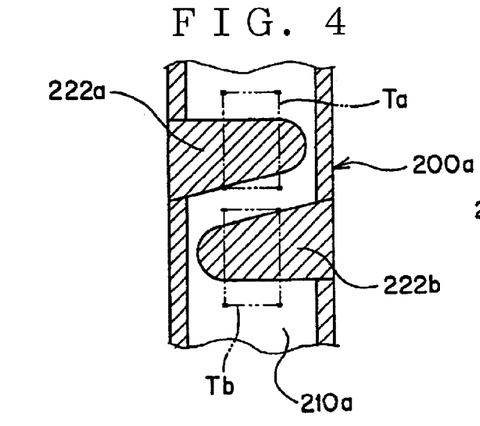
FIG. 4 is a schema showing the binary image of FIG. 3 and inspection areas.

The binary processing makes a binary image having picture elements of white or black. The control unit 7 calculates the number of black picture elements in predetermined inspection areas Ta, Tb (FIG. 4). Here, in the binary processing, a picture element of less than the threshold value is called a black picture element, and a picture element of not less than the threshold value is called a white picture element.

The crimping pieces 212a, 212b are provided with the respective inspection areas which are at least partial images of the whole images of the respective normally crimped crimping pieces 212a, 212b of the wire connecting portion 204. As shown in FIG. 4, the inspection areas is rectangular and provided on the longitudinal center of the wire connecting portion 204.

And, the control unit 7 prestores positional relation between a characteristic point such as a corner of the connector housing 201 and the inspection areas Ta, Tb. The control unit 7 extracts the above characteristic point from the image of the wire connecting portion 204 of the above pressure welding terminal 200, and subsequently establishes the inspection areas Ta, Tb in the above binary image on the basis of the prestored positional relation. Here, an area, a form, and a position of each of the above inspection areas Ta, Tb is suitably determined according to article numbers and the like of the pressure welding terminal 200 as the inspection object.

The control unit 7 judges whether the number of the black picture elements of each of the inspection areas Ta, Tb is not less than the predetermined reference value. The control unit 7 judges the inspection article to be the non-defective with the crimping pieces 212a, 212b having been normally crimped when the result is not less than the reference value. The control unit 7 judges the defective with the crimping pieces 212a, 212b having not been normally crimped when the result is less than the reference value.

The above-described inspection system 1 is used, for example, in the pressure welding apparatus shown in Japanese Patent Application Laid-open No.10-154568 or arranged near the above pressure welding apparatus. After the pressure welding apparatus pressure-welds the electric wire 210 to the pressure welding terminal 200 inserted in the terminal accommodating groove 202 of the connector housing 201, the inspection system 1 inspects the fastening condition of the electric wire 210 by the crimping pieces 212a,212b, that is, the bending condition of the crimping pieces 212a,212b.

Figure 9:
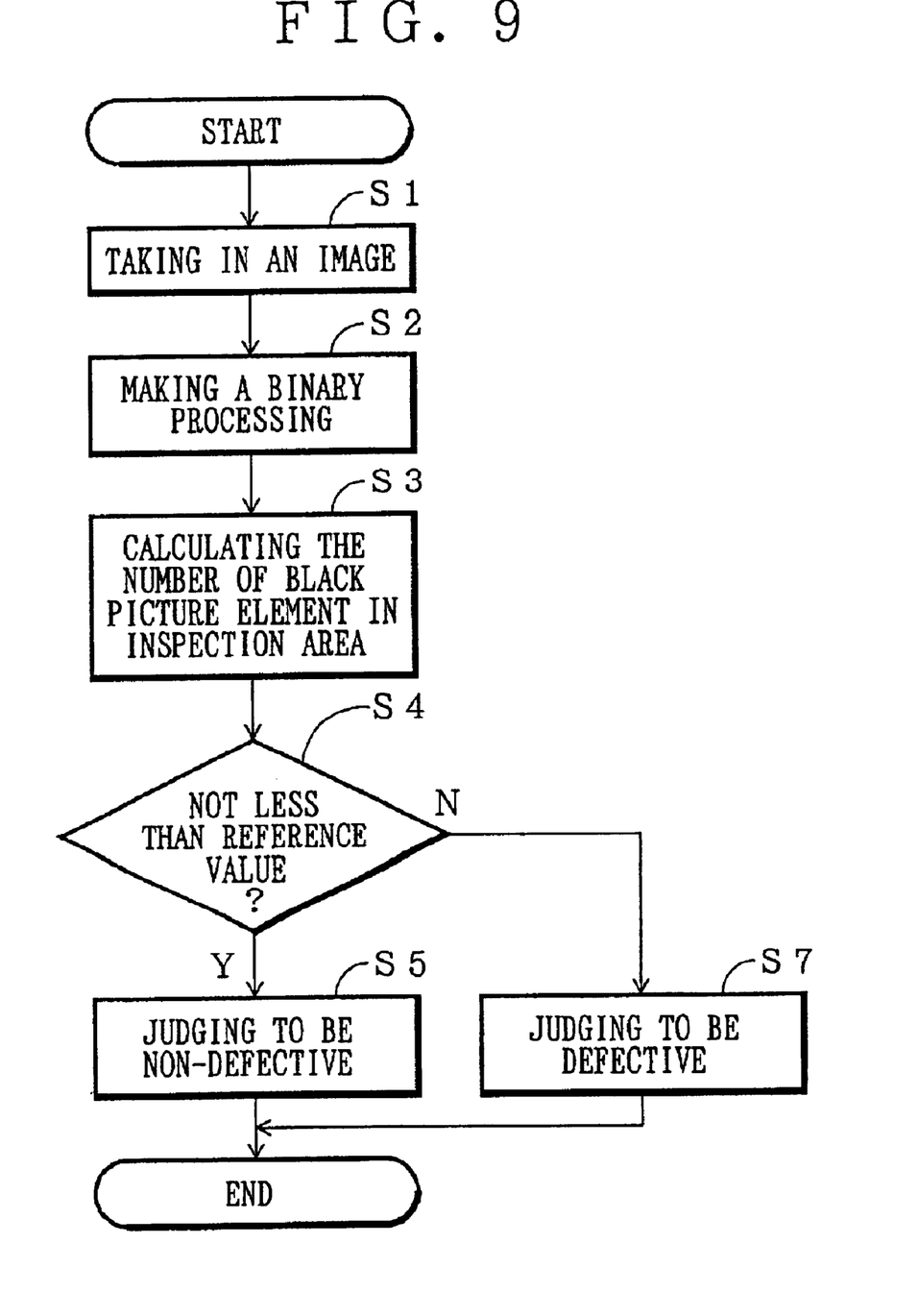
FIG. 9 is a flowchart of the inspection by the inspection system of FIG. 1.

When the pressure welding terminal 200 is inspected with the inspection system 1 of the present embodiment, the CCD camera 5 image-takes the wire connecting portion 204 of the pressure welding terminal 200 firstly in Step S1 in FIG. 9, and the image is outputted to the control unit 7. The control unit 7 stores the image information from the CCD camera 5 once, and Step S2 is reached.

The image information in this Step S1 is two-dimensional digital image information having the light intensity of 256 levels.

Here, because the light, from the illuminating lamp 4, reflected by the crimping pieces 212a, 212b does not enter the CCD camera 5, the inner surface of the dark box 6 is reflected in the pressure welding terminal 200 with the crimping pieces 212a, 212b and therefore the crimping pieces 212a, 212b become relatively black. And, the electric wire 210 and the connector housing 201 become relatively white because the electric wire 210 is a light color and the connector housing 201 is white.

Figure 3:
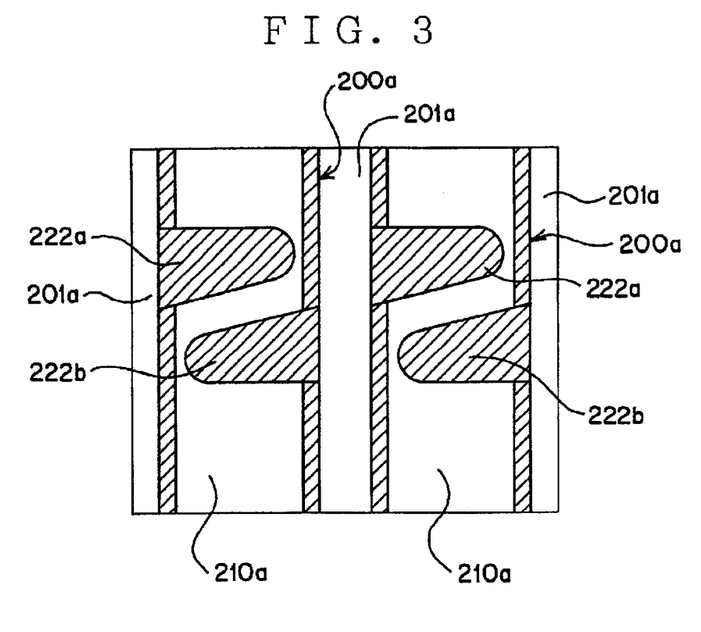
FIG. 3 is a schema showing a binary image of normally crimped crimping pieces taken by a CCD camera of the inspection system shown in FIG. 1.

In Step S2, the control unit 7 carries out the binary processing by using the predetermined threshold value for the image information from the CCD camera 5, and Step S3 is reached. In the binary image, as the image information, obtained by the binary processing, the portion 200a showing the pressure welding terminal 200 is black as shown in FIG. 3, and the portions 201a,210a showing the connector housing 201 and the electric wire 210 respectively is white. Here, in FIG. 3 and FIG. 4 to FIG. 8, the portion 200a in black in the binary image is designated by dense parallel oblique lines.

In Step S3, the control unit 7 calculates the number of the black picture elements in the inspection areas Ta, Tb (FIG. 4) in the above binary image, and Step S4 is reached. Like this, in Step S3, the control unit 7 calculates an area of black (an area less than the threshold value) of the inspection areas Ta, Tb, that is, the crimping pieces 212a,212b.

In Step S4, the control unit 7 judges whether the picture element number calculated in Step S3 is not less than the reference value. When it is not less than the reference value, Step S7 is reached, and when it is less than the reference value, the process goes to Step S5. In Step S5, the control unit 7 judges the pressure welding terminal 200 to be the non-defective in which the crimping pieces 212a, 212b of the wire connecting portion 204 are normally crimped. In Step S7, the control unit 7 judges the pressure welding terminal 200 to be the defective in which the crimping pieces 212a, 212b of the wire connecting portion 204 are not normally crimped.

Like this, in the inspection system 1 of the present embodiment, the control unit 7 calculates an area in black in the inspection areas Ta, Tb, namely an area becoming black of the crimping pieces 212a, 212b. On the basis of this calculated area, the good or bad of the fastening condition of the electric wire 210 by the crimping pieces 212a, 212b is judged. Otherwise, an area in white in the inspection areas Ta, Tb (an area not less than the threshold value) may be calculated so as to judge the good or bad of the fastening condition.

According to the present embodiment, the illuminating lamp 4 is arranged at a position of making the angle θ being not more than 45 degrees. Because the light, from the illuminating lamp 4, reflected by the crimping pieces 212a, 212b does not enter the CCD camera 5, the inner surface of the dark box 6 is reflected in the pressure welding terminal 200 with the crimping pieces 212a, 212b. And, the sheathing portion of the electric wire 210 is a light color.

Therefore, the portion 210a showing the electric wire 210 securely becomes white and the portions 222a, 222b showing the crimping pieces 212a, 212b become black as shown in FIG. 3 to FIG. 8 when the image of the wire connecting portion 204 obtained by the CCD camera 5 is binary-processed. Accordingly, the portion 210a showing the electric wire 210 and the portions 222a, 222b showing the crimping pieces 212a, 212b can be securely distinguished.

Figure 5:
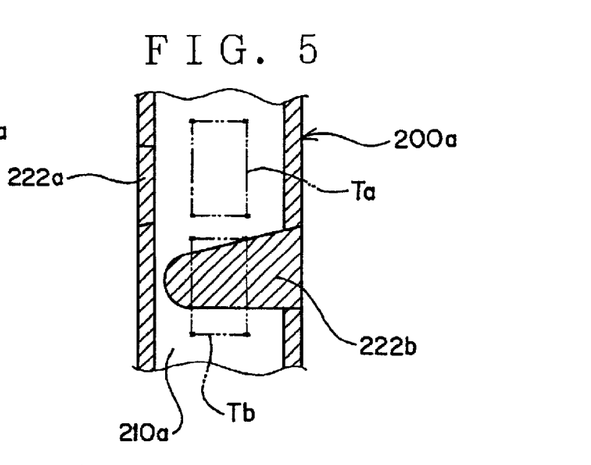
FIG. 5 is a schema showing a binary image of a crimping failure with one crimping piece.

Therefore, a state that the crimping piece 212a is stood as shown in FIG. 5 and a state that the crimping pieces 212a, 212b are bent and fastening the electric wire 210 as shown in FIG. 4 can be easily distinguished for example.

Figure 6:
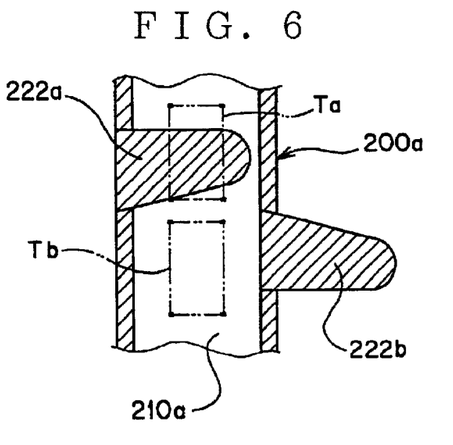
FIG. 6 is a schema showing a binary image of another crimping failure with one crimping piece.

And, a state that the crimping pieces 212b is bent outwardly of the wire connecting portion 204 as shown in FIG. 6 and a state that the crimping pieces 212a, 212b are bent toward the wall 208 and fastening the electric wire 210 as shown in FIG. 4 can be easily distinguished.

Accordingly, on the basis of an area in white or black (not less than or less than the threshold value) in the binary image, the good or bad of the fastening condition of the electric wire 210 by the crimping pieces 212a, 212b can be securely judged.

Further, the fastening condition of the electric wire 210 by each of the crimping pieces 212a, 212b is judged on the basis of whether or not an area in black in each of the inspection areas Ta, Tb provided for the respective crimping pieces 212a, 212b is not less than the reference value. When the crimping piece is in crimping failure as shown in FIG. 5 and FIG. 6, an area in black almost does not occur in the inspection area.

Like this, by providing the inspection area for each crimping piece, the fastening condition of the electric wire 210 can be more unerringly judged than a case of providing one large inspection area over a plurality of crimping pieces 212a, 212b, even if the reference value is a relatively small one of, for example, 10% of each of the inspection areas Ta, Tb.

And, in the pressure welding work, a film of the sheathing portion of resin often sticks to the crimping piece having been normally crimped. In this case, a white portion may arise in the portion 222b of the binary image showing the crimping piece 212b as shown in FIG. 7.

Figure 7:
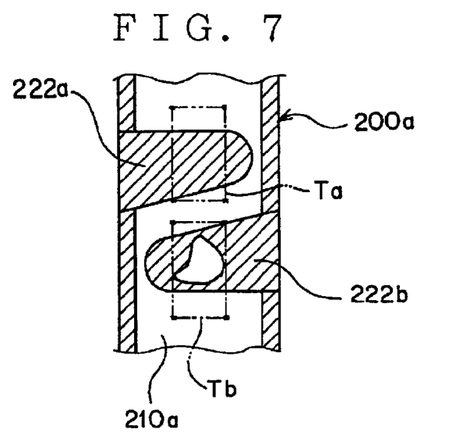
FIG. 7 is a schema showing a binary image of a state of a film of a sheathing portion of synthetic resin sticking to the crimping piece having been normally crimped.

Even in the case of FIG. 7, the normally crimped crimping piece 212b with the film can be judged to be non-defective by making the reference value relatively small. Like this, the fastening condition of the electric wire 210 can be unerringly judged.

Further, in pressure welding work, an unevenness may be formed on the surface of the crimping pieces 212a, 212b. In this case, the light from the illuminating lamp 4 reflects irregularly on the crimping pieces 212a, 212b, and therefore white portions would arise in the portions 222a, 222b showing the crimping pieces 212a, 212b in the binary image as shown in FIG. 8.

Figure 8:
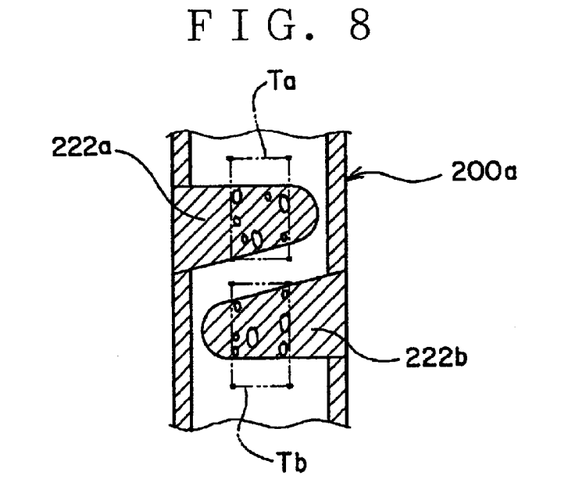
FIG. 8 is a schema showing a binary image of a state of irregular reflection on the crimping pieces having been normally crimped.

Even in such a case of FIG. 8, similarly to the case of FIG. 7, the normally crimped crimping pieces 212a, 212b irregularly reflecting the light from the illuminating lamp 4 can be judged to be non-defective by making the reference value relatively small. Like this, the fastening condition of the electric wire 210 can be unerringly judged.

The above inspection areas Ta, Tb are positioned over the lateral center of the electric wire 210. That is, the inspection areas Ta, Tb are arranged at positions ensuring the binary images thereof to sensitively show black or white according to the good or bad of the crimping thereof.

Therefore, the portion 210a showing the electric wire 210 of the binary image and the portions 222a, 222b showing the crimping pieces 212a, 212b can be still more securely distinguished. Accordingly, based on an area in white or black in the binary image, the good or bad of the fastening condition of the electric wire 210 by the crimping pieces 212a, 212b can be securely judged.

Next, an inspection system 1 in accordance with a second embodiment of the present invention is described by making reference to FIG. 11 to FIG. 19. Hereinafter, the same characters are assigned to the same elements as those of the first embodiment, and the description is omitted.

Figure 11:
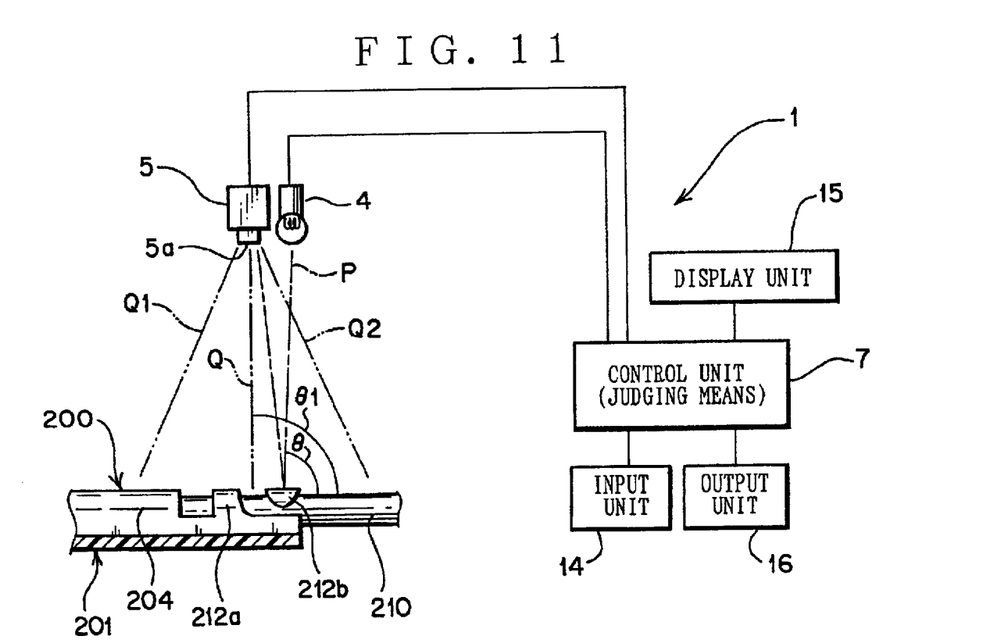
FIG. 11 is a schematic diagram showing the structure of a inspection system of a terminal metal fitting in accordance with a second embodiment of the present invention.
Figure 12:
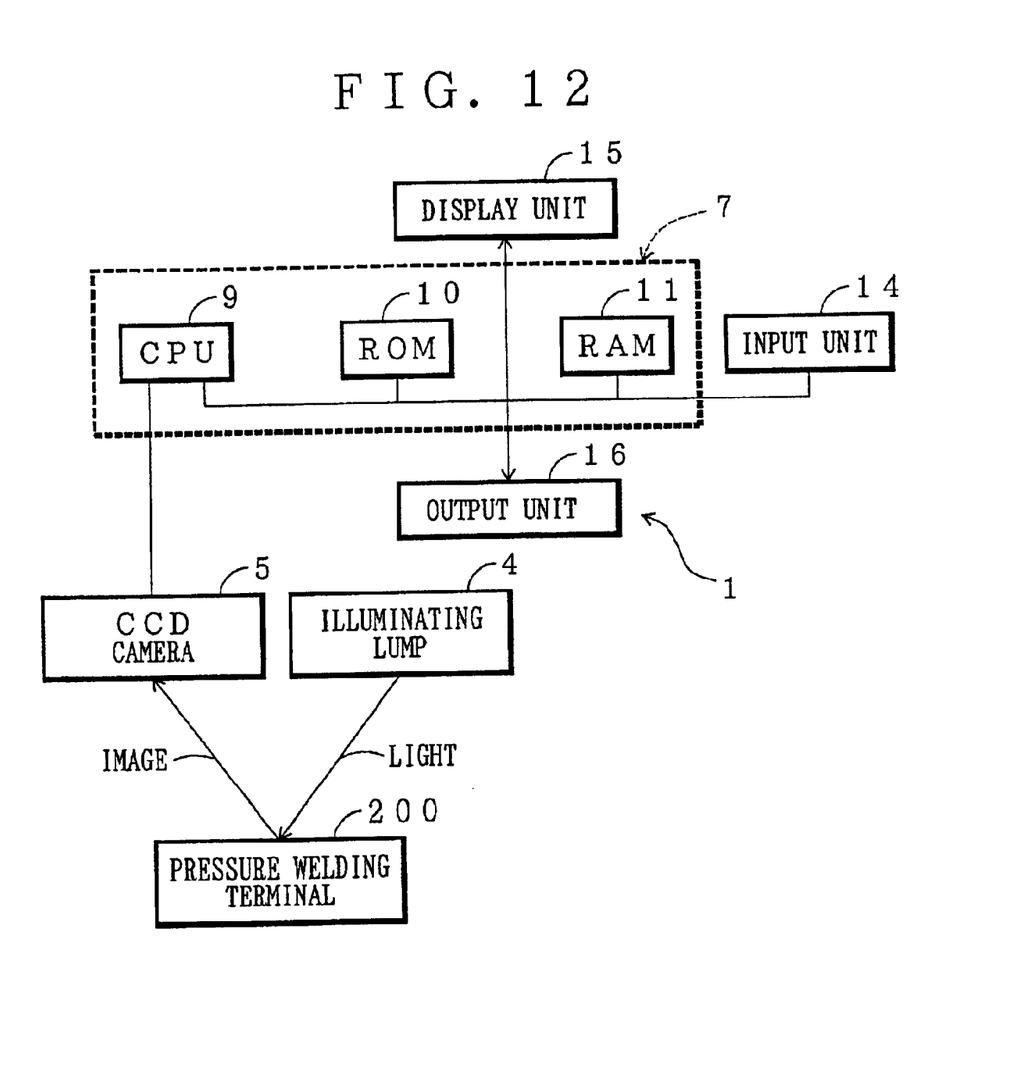
FIG. 12 is a block diagram of the inspection system shown in FIG. 11.

The inspection system 1 of the present embodiment, as shown in FIG. 11 and FIG. 12, does not use the dark box 6, and the illuminating lamp 4 is arranged at a position facing the wall 208 and the crimping pieces 212a, 212b having been normally crimped. The illuminating lamp 4 is arranged near the CCD camera 5. The illuminating lamp 4 is arranged at a position where the angle θ between the optical axis P and the wall 208 is almost 90 degrees. And, in the present embodiment, the sheathing portion of the electric wire 210 does not need to be a light color, that is, any color is applicable.

In the present embodiment, the light from the illuminating lamp 4 reflected by the crimping pieces 212a, 212b of the pressure welding terminal 200 as an inspection object enters the CCD camera 5 as shown in FIG. 11 and FIG. 12.

The control unit 7 of the present embodiment takes in the image of the wire connecting portion 204 taken by the CCD camera 5 and saves it. Here, the image is the digital image similarly to the above first embodiment. The control unit 7 carries out the binary processing with a predetermined threshold value on the image of the wire connecting portion 204. Here, this threshold value is suitably determined similarly to the first embodiment.

Figure 14:
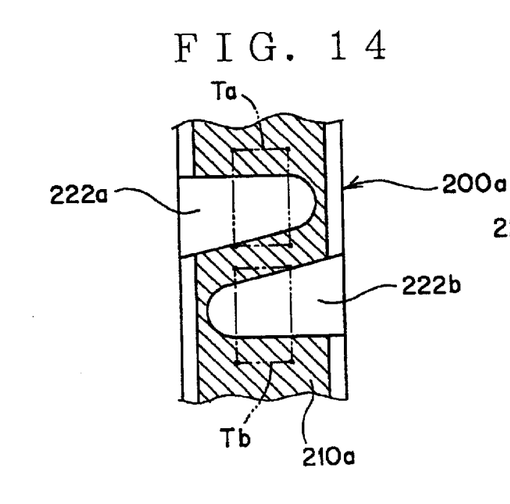
FIG. 14 is a schema showing the binary image of FIG. 13 and inspection areas.

The control unit 7 calculates the number of white picture elements in predetermined inspection areas Ta, Tb (FIG. 14).

The control unit 7 judges whether the number of the white picture elements of each of the inspection areas Ta, Tb is not less than the predetermined reference value. The control unit 7 judges the inspection article to be the non-defective with the crimping pieces 212a, 212b having been normally crimped when the result is not less than the reference value. The control unit 7 judges the inspection article to be the defective with the crimping pieces 212a, 212b having not been normally crimped when the result is less than the reference value.

Figure 19:
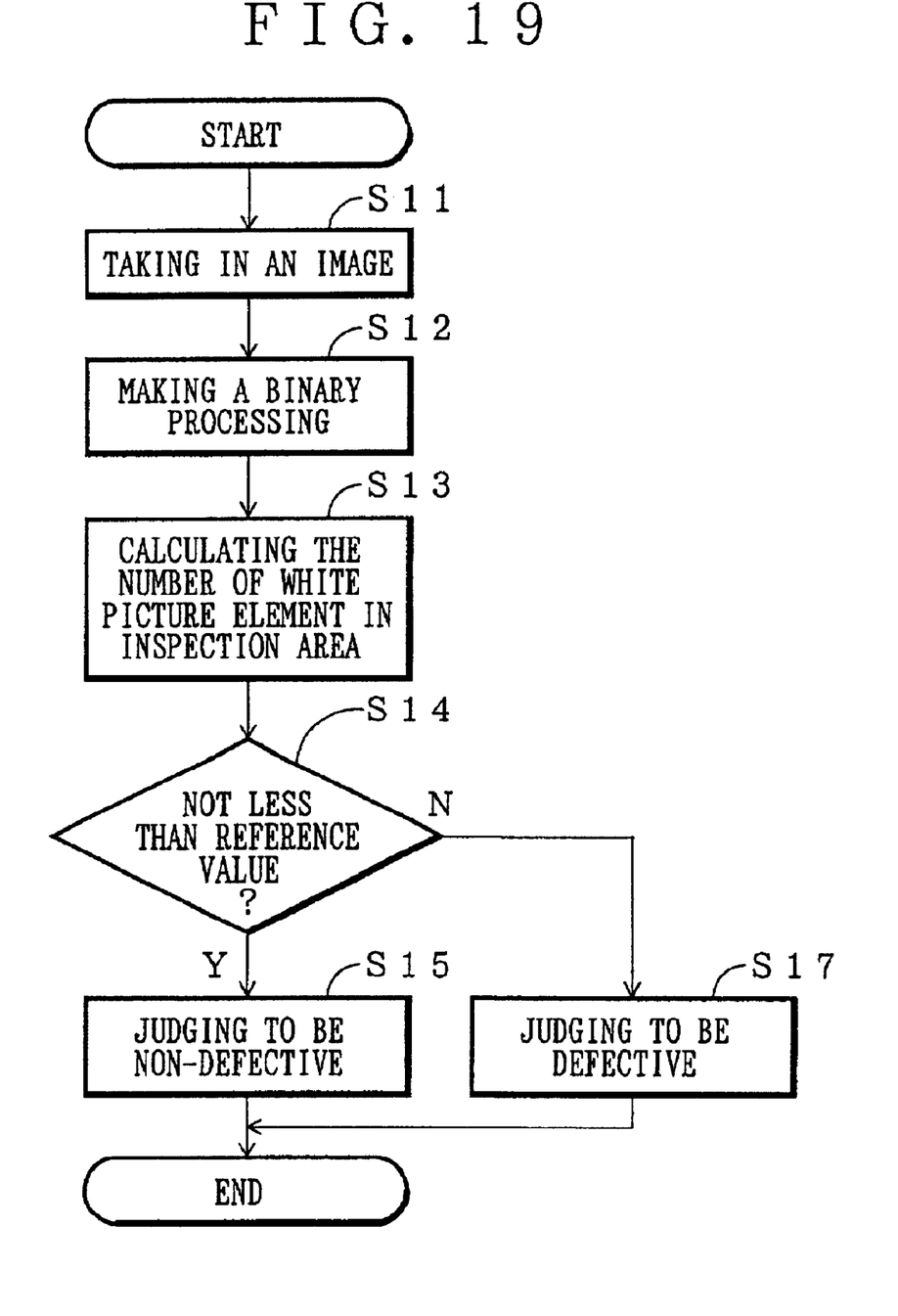
FIG. 19 is a flowchart of the inspection by the inspection system of FIG. 11.

The inspection system 1 of the present embodiment judges the good or bad of the fastening condition of the electric wire 210 by the crimping pieces 212a, 212b along the flowchart shown in FIG. 19. First, in Step S11 in FIG. 19, the CCD camera 5 takes the image of the wire connecting portion 204 of the pressure welding terminal 200, the control unit 7 stores the image information from the CCD camera 5, and Step S12 is reached.

In this Step S11, the image information taken by the CCD camera 5 and stored in the control unit 7 is two-dimensional digital image information. Here, because the CCD camera 5 is arranged at the position where the light from the illuminating lamp 4 reflected by the crimping pieces 212a, 212b enters the CCD camera 5, the pressure welding terminal 200 including the crimping pieces 212a, 212b reflects the light from the illuminating lamp 4 and becomes relatively white. And, the electric wire 210 and the connector housing 201 become relatively black.

Figure 13:
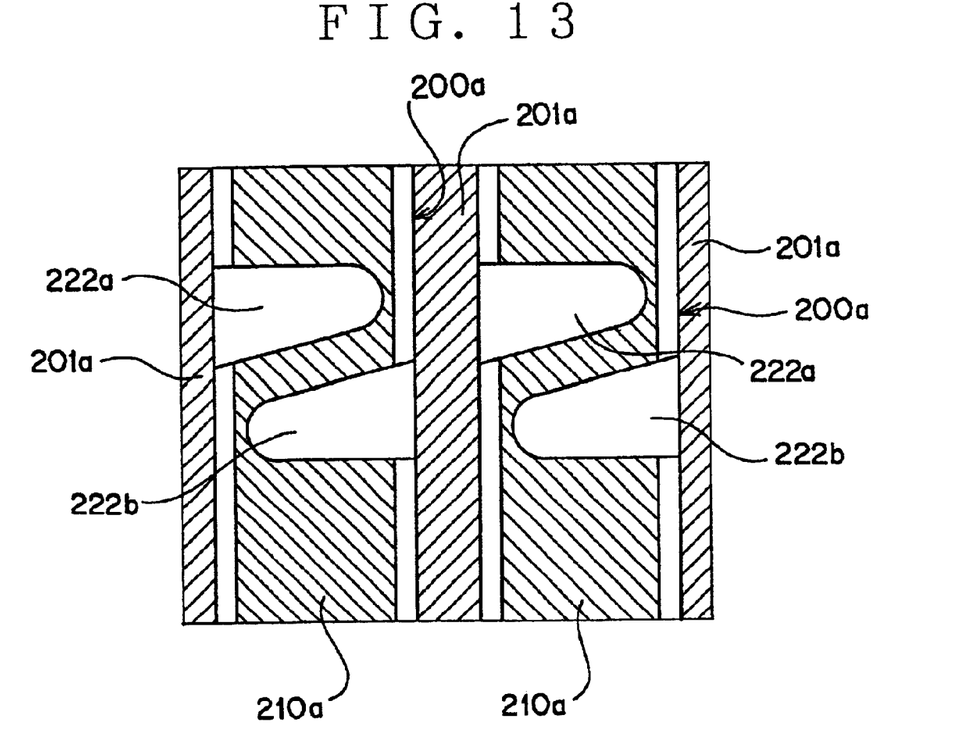
FIG. 13 is a schema showing a binary image of normally crimped crimping pieces taken by a CCD camera of the inspection system shown in FIG. 11.

In Step S12, the control unit 7 carries out the binary processing by using a predetermined threshold value for the image information from the CCD camera 5, and Step S13 is reached. In the above binary image obtained by the binary processing, as shown in FIG. 13, the portion 200a showing the pressure welding terminal 200 becomes white, and the portions 201a, 210a showing the connector housing 201 and the electric wire 210 respectively become black. Here, in FIG. 13 and FIG. 14 to FIG. 18, the portions 201a, 210a in black in the binary image are designated by dense parallel oblique lines.

In Step S13, the control unit 7 calculates the number of the white picture elements in the inspection areas Ta, Tb (FIG. 4) in the above binary image, and Step S14 is reached. In Step S14, the control unit 7 judges whether the number of the picture elements calculated in Step S13 is not less than the reference value.

The process goes to Step S15 when the result is not less than the reference value, and the process goes to Step S17 when the result is less than the reference value. In Step S15, the control unit 7 judges the pressure welding terminal 200 being an inspection object to be non-defective. In Step S17, the control unit 7 judges the pressure welding terminal 200 to be defective.

Like this, in the inspection system 1 of the present embodiment, the control unit 7 calculates an area in white (an area not less than the threshold value) in the inspection areas Ta, Tb, namely an area becoming white of the crimping pieces 212a, 212b. On the basis of this calculated area, the good or bad of the fastening condition of the electric wire 210 by the crimping pieces 212a, 212b is judged. Otherwise, an area in black in the inspection areas Ta, Tb may be calculated so as to judge the good or bad of the fastening condition.

According to the present embodiment, the illuminating lamp 4 is arranged near the CCD camera 5. The light, from the illuminating lamp 4, reflected by the crimping pieces 212a, 212b enters the CCD camera 5. That is, the pressure welding terminal 200 including the crimping pieces 212a, 212b shines, while reflecting the light from the illuminating lamp 4, viewing from the CCD camera 5.

Therefore, the portion 210a showing the electric wire 210 securely becomes black and the portions 222a, 222b showing the crimping pieces 212a, 212b become white as shown in FIG. 13 to FIG. 18 when the image of the wire connecting portion 204 obtained by the CCD camera 5 is binary-processed. Accordingly, the portion 210a showing the electric wire 210 and the portions 222a, 222b showing the crimping pieces 212a, 212b can be securely distinguished.

Figure 15:
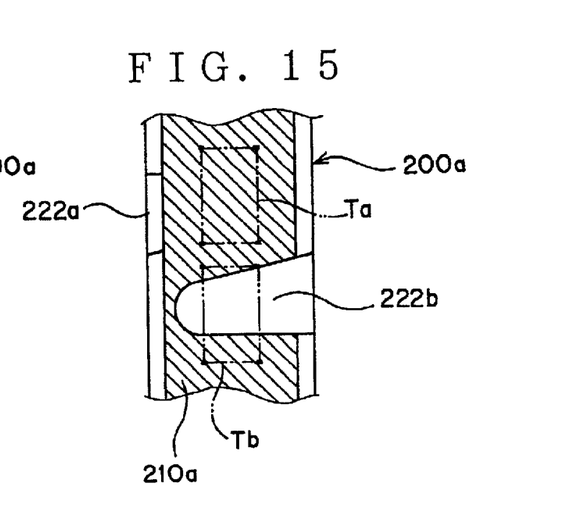
FIG. 15 is a schema showing a binary image of a crimping failure with one crimping piece.

Therefore, a state that the crimping piece 212a is stood as shown in FIG. 15 and a state that the crimping pieces 212a, 212b are bent and fastening the electric wire 210 as shown in FIG. 14 can be easily distinguished for example.

Figure 16:
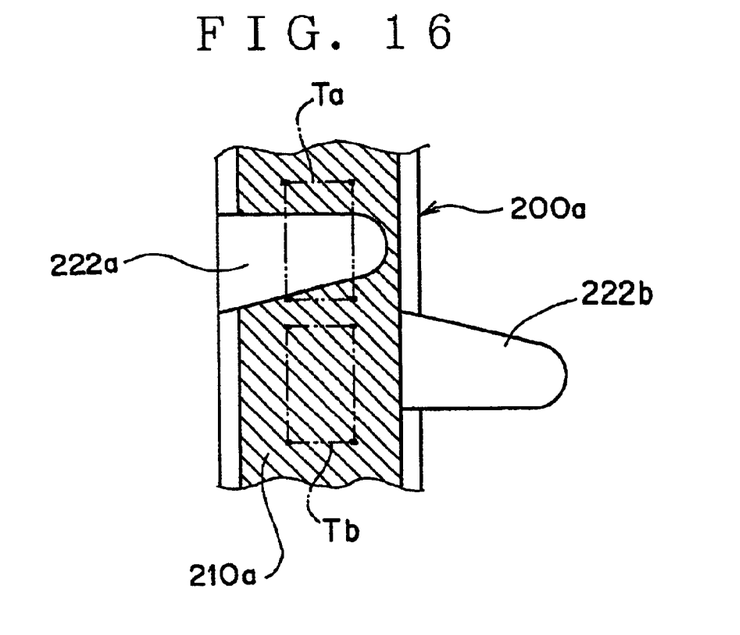
FIG. 16 is a schema showing a binary image of another crimping failure with one crimping piece.

And, a state that the crimping pieces 212b is bent outwardly of the wire connecting portion 204 as shown in FIG. 16 and a state that the crimping pieces 212a, 212b are bent toward the wall 208 and fastening the electric wire 210 as shown in FIG. 14 can be easily distinguished.

Accordingly, on the basis of an area in white or black in the binary image, the good or bad of the fastening condition of the electric wire 210 by the crimping pieces 212a, 212b can be securely judged.

Further, the fastening condition of the electric wire 210 by each of the crimping pieces 212a, 212b is judged on the basis of whether or not an area in white in each of the inspection areas Ta, Tb provided for the respective crimping pieces 212a, 212b is not less than the reference value. When the crimping piece is in crimping failure as shown in FIG. 15 and FIG. 16, an area in white almost does not occur in the inspection area.

Like this, by providing the inspection area for each crimping piece, the fastening condition of the electric wire 210 can be more unerringly judged than a case of providing one large inspection area over a plurality of crimping pieces 212a, 212b, even if the reference value is a relatively small one of, for example, 10% of each of the inspection areas Ta, Tb.

And, in the pressure welding work, a film of resin of the sheathing portion often sticks to the crimping piece having been normally crimped. In this case, a black portion may arise in the portion 222b of the binary image showing the crimping piece 212b as shown in FIG. 17.

Figure 17:
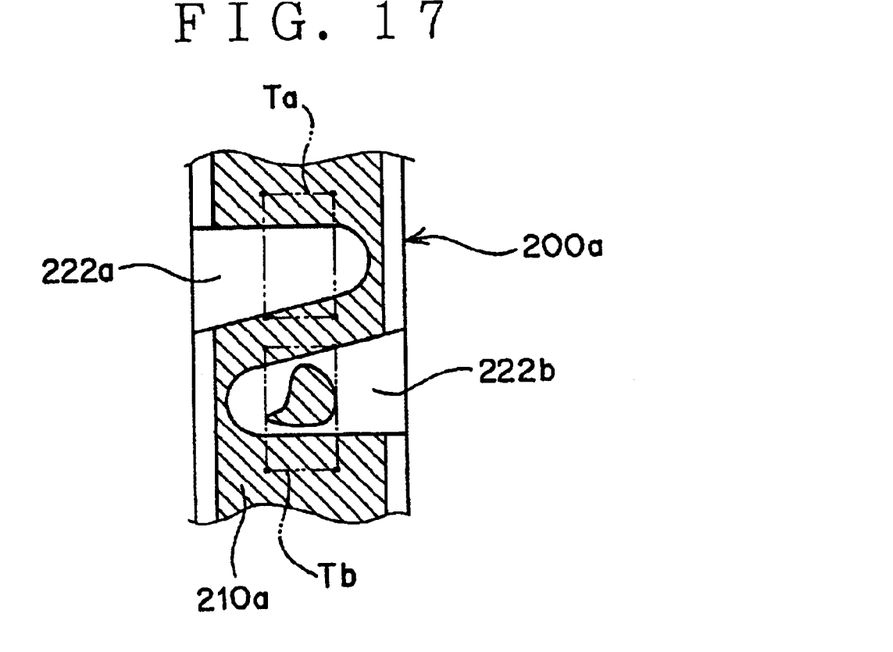
FIG. 17 is a schema showing a binary image of a state of a film of a sheathing portion of synthetic resin sticking to the crimping piece having been normally crimped.

Even in the case of FIG. 17, the normally crimped crimping piece 212b with the film can be judged to be non-defective by making the reference value relatively small. Like this, the fastening condition of the electric wire 210 can be unerringly judged.

Further, in pressure welding work, an unevenness may be formed on the surface of the crimping pieces 212a, 212b. In this case, the light from the illuminating lamp 4 reflects irregularly on the crimping pieces 212a, 212b, and therefore black portions would arise in the portions 222a, 222b showing the crimping pieces 212a, 212b in the binary image as shown in FIG. 18.

Figure 18:
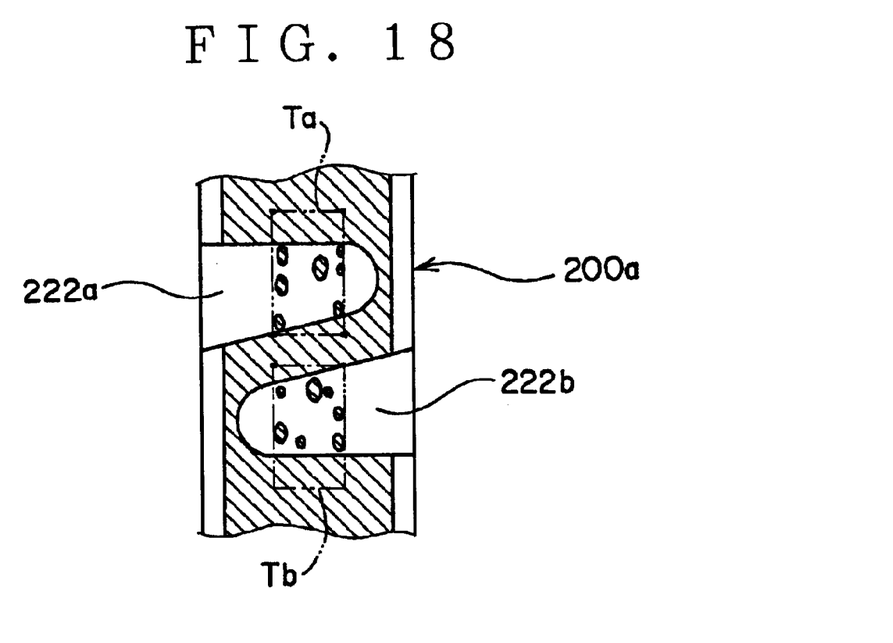
FIG. 18 is a schema showing a binary image of a state of irregular reflection on the crimping pieces having been normally crimped.

Even in such a case of FIG. 18, similarly to the case of FIG. 17, the normally crimped crimping pieces 212a, 212b irregularly reflecting the light from the illuminating lamp 4 can be judged to be non-defective by making the reference value relatively small. Like this, the fastening condition of the electric wire 210 can be unerringly judged.

The above inspection areas Ta, Tb are positioned in the lateral center of the electric wire 210. That is, the inspection areas Ta, Tb are arranged at positions ensuring the binary images thereof to show black or white in accordance to poor or good of the crimping thereof.

Therefore, the portion 210a showing the electric wire 210 of the binary image and the portions 222a, 222b showing the crimping pieces 212a, 212b can be still more securely distinguished. Accordingly, based on an area in white in the binary image, the good or bad of the fastening condition of the electric wire 210 by the crimping pieces 212a, 212b can be securely judged.

In the inspection system 1 of the above-described first and second embodiments, the wire connecting portion 204 of the pressure welding terminal 200 is illuminated, and the judgement of the good or bad thereof is carried out on the basis of the image of the crimping pieces 212a, 212b of the wire connecting portion 204. Because the terminal metal fitting 200 with the crimping pieces 212a, 212b is made of metal, the light is reflected well or an object facing the terminal metal fitting 200 is projected well.

Therefore, the intensity of the reflected light of the terminal metal fitting 200 and the electric wire 210 is different when the wire connecting portion 204 is illuminated. Therefore, by binary-processing the image of the above wire connecting portion 204, the crimping pieces 212a, 212b and the electric wire 210 can be distinguished.

Because states of the crimping pieces 212a, 212b, that is, standing perpendicularly to the wall 208, being bent outwardly of the wire connecting portion 204, and being bent inwardly toward the wall 208 while fastening the electric wire 210, can be easily distinguished, the good or bad of the fastening condition of the electric wire 210 by the crimping pieces 212a, 212b can be easily judged.

Though the inspection system 1 of the first and second embodiments inspect the fastening condition by the crimping pieces 212a, 212b of the pressure welding terminal 200, the inspection system of the terminal metal fitting of the present invention can be applied to crimping pieces of a crimp terminal.

Although the present invention has been fully described by way of examples with reference to the accompanying drawings, it is to be noted that various changes and modifications will be apparent to those skilled in the art. Therefore, unless otherwise such changes and modifications depart from the scope of the present invention, they should be construed as being included therein.

What is claimed is:

1. An inspection method of a terminal metal fitting having a wire connecting portion having a wall carrying a sheathed electric wire and a crimping piece with a mirror reflection surface bent toward the wall so as to fasten the electric wire between the crimping piece and the wall, comprising the steps of:

illuminating the wire connecting portion fastened to the electric wire from a first specific direction;

taking an image of the wire connecting portion from a second specific direction;

binary-processing the image of the wire connecting portion;

calculating whether an area is less than or not less than a threshold value in image information obtained by the binary processing; and     judging good or bad of a fastening condition of the electric wire by the crimping piece on a basis of the area.

2. An inspection system of a terminal metal fitting having a wire connecting portion having a wall carrying an electric wire and a crimping piece bent toward the wall so as to fasten the electric wire between the crimping piece and the wall, comprising:

a light source to illuminate the wire connecting portion;

an image-taking means to take an image of the wire connecting portion;

a dark box, with a dark inner surface, to cover at least an object side of the image-taking means, the light source, and the terminal metal fitting for preventing outer light from shining on the wire connecting portion; and     a judging means to binary-process an image of the wire connecting portion being illuminated by the light source and judge whether good or bad as to a fastening condition of the electric wire by the crimping piece on a basis of an area being less than or not less than a threshold value in image information obtained by the binary processing,     wherein the image-taking means and the light source are arranged so that the light thrown from the light source and reflected by the crimping piece with a mirror reflection surface does not enter the image-taking means, and a sheathing portion of the electric wire is a light color.

3. The inspection system of the terminal metal fitting as set forth in claim 2, wherein     the image-taking means faces the wall of the wire connecting portion to which the electric wire is fastened,     and the light source is arranged at a position of making an angle θ between a line connecting the light source with the crimping piece and a direction of the electric wire fastened to the wire connecting portion so that the light thrown from the light source and reflected by the crimping piece does not enter the image-taking means.

4. The inspection system of the terminal metal fitting as set forth in claim 3, wherein     the light source is arranged at a position of making the angle θ of not more than 45 degrees.

5. An inspection system of a terminal metal fitting having a wire connecting portion having a wall carrying an electric wire and a crimping piece bent toward the wall so as to fasten the electric wire between the crimping piece and the wall, comprising:

a light source to illuminate the wire connecting portion;

an image-taking means to take an image of the wire connecting portion;

a judging means to binary-process an image of the wire connecting portion illuminated by the light source and judge good or bad of a fastening condition of the electric wire by the crimping piece on a basis of an area being less than or not less than a threshold value in image information obtained by the binary processing,     wherein the image-taking means and the light source are arranged so that the light thrown from the light source and reflected by the crimping piece with a mirror reflection surface enters the image-taking means.

6. The inspection system of the terminal metal fitting as set forth in claim 5, wherein     the image-taking means faces the wall of the wire connecting portion to which the electric wire is fastened,     and the light source faces the wall of the wire connecting portion, to which the electric wire is fastened, near the image-taking means so that the light thrown from the light source and reflected by the crimping piece enters the image-taking means.

7. The inspection system of the terminal metal fitting as set forth in any one of claims 2–6, wherein the judging means judges whether good or bad as to a fastening condition of the electric wire on a basis of an area being less than or not less than a threshold value in an inspection area in the image of the wire connecting portion taken by the image-taking means, the inspection area being provided for each crimping piece and including at least partial image of the crimping piece.

8. The inspection system of the terminal metal fitting as set forth in claim 7, wherein     the inspection area is positioned over a longitudinal axis of the electric wire fastened to the wire connecting portion.

* * * * *